United States Patent [19]
Kaplan et al.

[11] Patent Number: 5,571,948
[45] Date of Patent: Nov. 5, 1996

[54] PRESSURIZED AIR TANK AIR QUALITY TESTER

[75] Inventors: Lawrence Kaplan, Miami Beach; Robert Laughlin, Miami, both of Fla.

[73] Assignee: Lawrence Factor, Inc., Hialeah, Fla.

[21] Appl. No.: 445,756

[22] Filed: May 22, 1995

[51] Int. Cl.$^6$ .................................................. G01N 37/00
[52] U.S. Cl. ................ 73/31.05; 73/31.03; 128/205.23; 128/202.22; 128/202.27; 422/56; 422/58; 422/59; 422/86; 436/134
[58] Field of Search .................. 73/31.05, 863.25, 73/31.01, 31.02, 31.03, 31.07; 422/56, 58, 59, 83, 85, 88, 86; 436/134, 169; 128/202.22, 202.27, 205.23

[56] References Cited

U.S. PATENT DOCUMENTS

| | | | |
|---|---|---|---|
| 2,234,499 | 3/1941 | McAllister | 73/31.05 |
| 3,266,869 | 8/1966 | Dengler | 128/205.23 |
| 3,286,506 | 11/1966 | Lloyd | 73/31.05 |
| 3,372,274 | 3/1968 | Landolt . | |
| 3,388,975 | 6/1968 | Wallace | 436/134 |
| 4,073,619 | 2/1978 | Lawson . | |
| 4,389,372 | 6/1983 | Lalin | 422/88 |
| 4,576,054 | 3/1986 | Lalin . | |
| 4,728,499 | 3/1988 | Fehder | 422/56 |
| 4,994,117 | 2/1991 | Fehder | 422/85 |
| 5,174,964 | 12/1992 | Klodowski et al. | 422/58 |
| 5,291,879 | 3/1994 | Babb et al. | 128/205.23 |
| 5,417,204 | 5/1995 | Moesle, Jr. . | |

FOREIGN PATENT DOCUMENTS 1465738  3/1989  U.S.S.R. ............... 73/31.02

OTHER PUBLICATIONS

Mine Safety Appliances Co., "The M.S.A. Carbon Monoxide Detector", Bulletin No. BF–1, 20 Jan. 1936.
Shepard et al., "Determination of Carbon Monoxide in Air Pollution Studies", Analytical Chemistry, vol. 27, No. 3, Mar. 1955, pp. 380–383.

*Primary Examiner*—Hezron E. Williams
*Assistant Examiner*—Daniel S. Larkin
*Attorney, Agent, or Firm*—Malin, Haley, DiMaggio & Crosby, PA

[57] ABSTRACT

A pressurized air tank air quality tester comprising a housing having a longitudinal bore disposed therein. The housing has at least one closure disposed on at least one of the ends of the housing for sealing the housing and forming an airtight test chamber therein. A valve connector is connected to one of the ends of the housing for fluidly communicating the pressurized air source with the test chamber. An indicating cartridge is removably disposed within the test chamber for indicating by color an excessive amount of a contaminant contained within the test chamber.

16 Claims, 3 Drawing Sheets

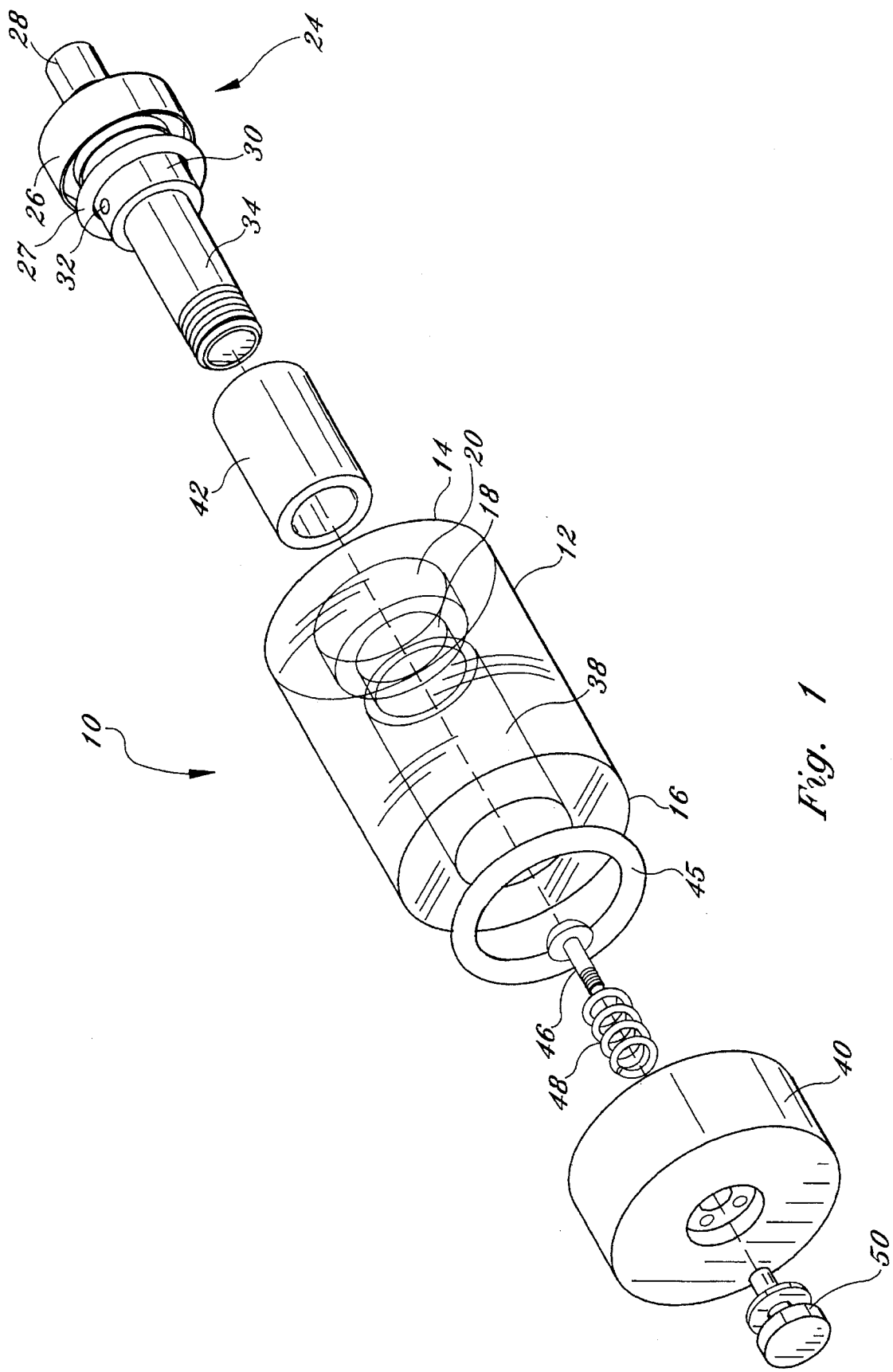

PRESSURIZED AIR TANK AIR QUALITY TESTER

BACKGROUND OF THE INVENTION

1. Field of the Invention

This invention relates to an air quality tester, and more particularly to a pressurized air tank air quality tester wherein an indicating cartridge for indicating by color the presence of an excessive amount of a given substance is disposed within a chamber in a housing that is attached to a pressurized air source.

2. Description of the Prior Art

The use of compressed breathing air in scuba tanks for scuba diving is well known. Most scuba tanks maintain compressed breathing air at 3000 psi for use when diving. Since the compressed air is directly utilized and provides the only source of air for the diver, the air source must be free of deleterious contaminants and must contain the proper mixture of nitrogen and oxygen to insure safe breathing for the diver. Compressed air bottles and tanks are also used by firefighting personnel for a source of breathing air in, smoked filled areas. Therefore, it is imperative that the air be free of contaminants and in the proper ratios of nitrogen and oxygen to insure safe, healthy breathing.

Scuba tanks and firefighting air tanks are periodically refilled from sources of air/gas stored in large, high pressure tanks or from compressor systems. The source of air is typically provided by commercial establishments for filling scuba and firefighter tanks. In order to insure that the air is of proper quality, it is necessary for these commercial establishments to periodically analyze air samples obtained from these large, pressurized storage tanks. This is done by collecting the air samples from each supply tank of pressurized compressed air/gas and sending them to outside laboratories for testing. It is essential that the sample testing be done correctly and accurately and that the retrieved samples be stored in containers or environments suitable for shipment to laboratory test sites. Moreover, it is commercially important for businesses that sample collection methods be kept simple and efficient to increase reliability and to decrease costs since frequent sampling of the air/gas source is required.

Heretofore, sampling kits have been directed toward the commercial establishment large, high pressure storage tanks. U.S. Pat. No. 3,372,274, issued to R. R. Landolt, Mar. 5, 1968, shows a gas sampler that collects inert radioactive fission gas. A float meter is shown to determine the amount of gas received into the system for proper analysis. U.S. Pat. No. 4,576,054, issued to H. S. Lalin, Mar. 18, 1986, shows a dual mode gas sampler and pneumatic float control system that allows simultaneous testing of gas samples for multiple test articles, either under constant pressure or, constant flow. The system shown includes an air pump and a regulating diaphragm. U.S. Pat. No. 4,073,619, issued to Lawson, Feb. 14, 1978, shows a device for sampling gas for analysis. Many of such prior art devices are complex in their structure and operation. Furthermore, these devices do not provide a small, portable air quality tester that may be connected directly to the scuba tanks and firefighting air tanks for testing the quality of the air inside the individual tanks.

Accordingly, the present invention provides a portable, compact air quality tester wherein the user is able to attach the device to the pressurized air source and observe, for a brief time, the indicating cartridge, wherein a change in color of the indicating cartridge indicates that the air inside the pressurized tank is contaminated.

SUMMARY OF THE INVENTION

The instant invention provides a pressurized air tank air quality tester that is connected directly to an individual pressurized air tank, such as a scuba tank or a firefighting air tank, for testing the quality of the air inside the individual tank. In its simplest embodiment, the apparatus comprises a housing having a longitudinal bore disposed therein, at least one closure disposed on at least one of the ends of the housing for sealing the housing and forming an airtight test chamber therein, a valve connector connected to one of the ends of the housing for fluidly communicating the pressurized air source with the test chamber, and an indicating cartridge removably disposed within the test chamber for indicating by color an excessive amount of a contaminant contained within the test chamber. In the preferred embodiment, the apparatus comprises a housing having an inlet end and an outlet end, the housing having a receding neck portion situated in the interiors volume defined by the housing, wherein the neck portion defines a passageway therethrough. The housing includes a countersunk portion forming a flange proximal the inlet end thereof, the flange defining a first side of the neck portion. The apparatus further includes a multi-tiered mounting shaft comprising a retaining hub situated between opposite ends of the mounting shaft, a valve connector integral with and disposed on one side of the retaining hub, a shank of lesser width than the width of the retaining hub, the shank extending inwardly from the side of the retaining hub opposite to that of the valve connector side. The shank comprises an aperture therethrough and a rod extending from the shank, the rod being of a lesser width than the shank, wherein the free end of the rod is threaded and defines one end of the mounting shaft. The mounting shaft further defines a bore extending from the valve connector to the shank aperture for fluidly communicating an outside pressurized air source with an interior test chamber defined by the base member, the mounting shaft, and the housing of the instant invention. The apparatus further comprises an indicating cartridge removably mounted on the rod for indicating by color the presence of an excessive amount of a given substance, such as carbon monoxide disposed within the interior test chamber. A base member is attached to the outlet end of the housing, the base member comprising a turret projection integrally formed in and extending axially inwardly from the base member and having a threaded aperture to engage the threaded end of the mounting shaft, the turret projection being of lesser width than the base member. A pressure relief valve is disposed in the base member. The multi-tiered mounting shaft is constructed such that the retaining hub is received by the flange proximal the inlet end of the housing and such that the aperture of the shank passes through the passageway in the neck portion, such that the top surface of the retaining hub is flush with the inlet end of the housing. An O-ring is disposed on the bottom side of the retaining hub, thereby sealably engaging the retaining hub with the flange. The base member contains an O-ring on an inner surface thereof for sealably engaging the base to the outlet end of the housing.

To utilize the invention, one would attach the valve connector of the instant invention to the pressurized air source and then open the valve from the air source to allow a short stream of compressed air to enter the interior test chamber via the valve connector and the bore extending from the valve connector to the shank aperture. After a few seconds, the valve from the air source is closed, whereupon a sample of the air from the air source is trapped within the interior test chamber along with the indicating cartridge. If the indicating cartridge changes color, then the user is notified by the color change that an excessive amount of a given substance, such as carbon monoxide, is present within the test chamber and also the compressed air source, therefore indicating that the compressed air source is contaminated and should not be used. The indicating cartridge utilizes a known indicating, color change material or gel and may be used to indicate carbon monoxide or any other contaminant. The indicating cartridge is removable and replaceable, and should be replaced preferably after ten to fifteen tests, or after contamination. The indicating cartridge is replaced by unscrewing the base member from the mounting shaft, and slidably removing the indicating cartridge from the mounting shaft.

It is an object of this invention to provide a pressurized air tank air quality tester that can quickly and accurately detect the presence of an excessive amount of a given substance.

And yet another object of this invention is to provide a pressurized air tank air quality tester wherein the device may be connected directly to a pressurized air tank for testing the quality of the air inside the individual tank.

In accordance with these and other objects which will become apparent hereinafter, the instant invention will now be described with particular reference to the accompanying drawings.

BRIEF DESCRIPTION OF THE DRAWINGS

FIG. 1 is an exploded view of one embodiment of the pressurized air tank air quality tester of the instant invention;

FIG. 2b is a sectional view taken along line 2b–2b of FIG. 2a;

DESCRIPTION OF THE PREFERRED EMBODIMENTS

Figures 2A, 3:
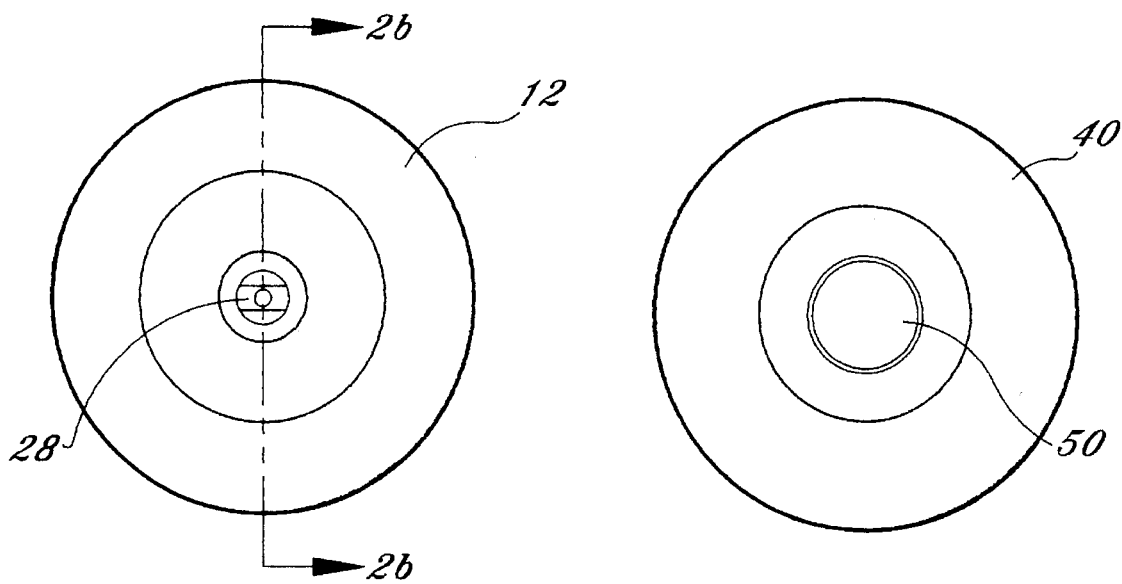
FIG. 2a is a top view of the embodiment shown in FIG. 1.
FIG. 3 is a bottom view of the embodiment shown in FIG. 1.

With reference to the drawings, FIGS. 1–4a depict a pressurized air tank air quality tester shown generally indicated by the reference numeral 10. Throughout the figures, like referenced characters are used to indicate like elements.

Figure 4:
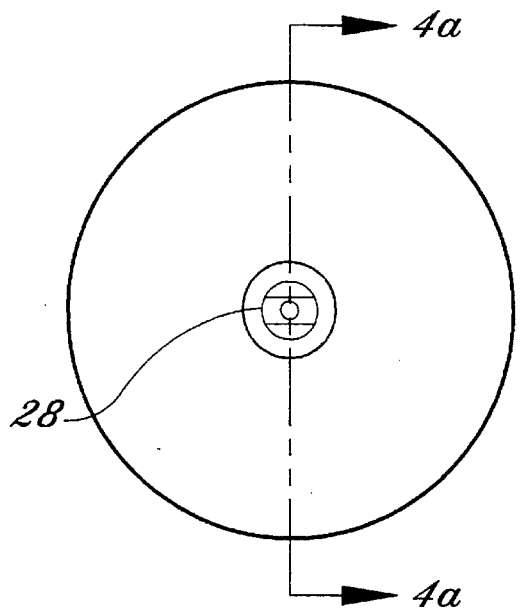
FIG. 4 is a top view of an alternate embodiment of the instant invention.
Figure 4A:
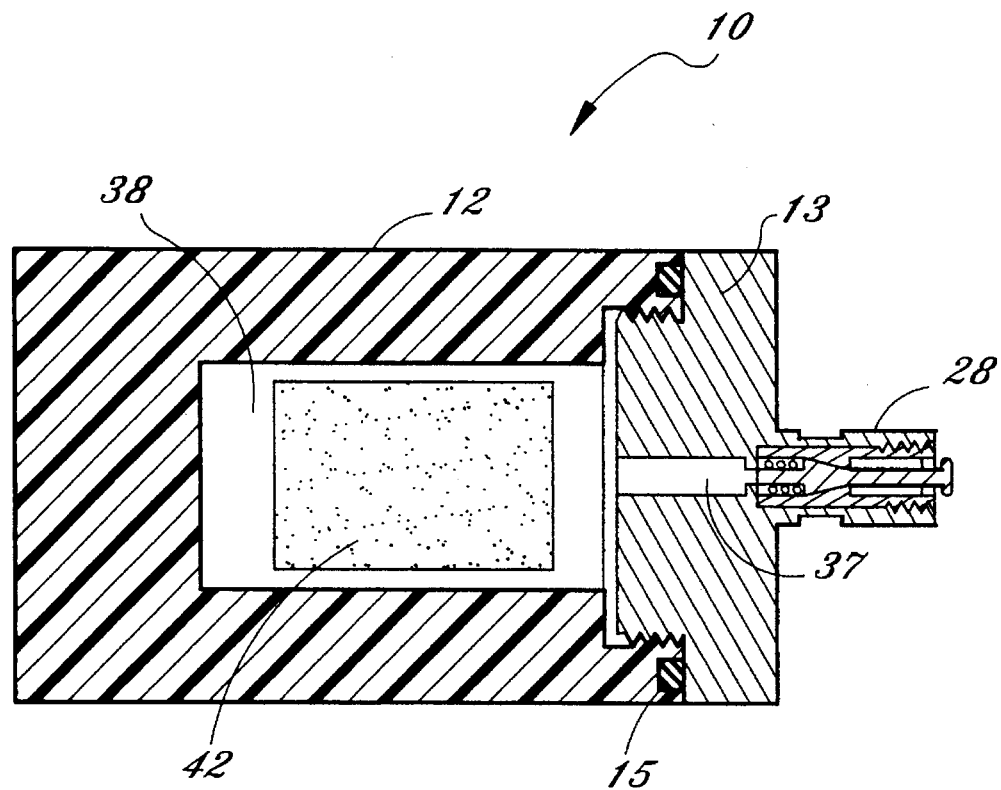
FIG. 4a is a sectional view taken along line 4a–4a of FIG. 4.

With reference to the drawing FIGS. 1–4a, and in particular FIG. 4a, the apparatus comprises a housing 12 having a longitudinal bore disposed therein. The housing 12 has at least one closure 13 disposed on at least one of the ends of the housing for sealing the housing 12 and forming an airtight test chamber 38 therein. The closure 13 has an O-ring 15 disposed on an inner surface thereof for sealingly engaging the closure 13 to the housing 12. A valve connector 28 is connected to one of the ends of the housing, and as shown in FIG. 4a, to the end of the housing 12 having closure 13. Closure 13 defines a bore 37 extending from the valve connector 28 to the test chamber 38 for fluidly communicating the pressurized air source (not shown) with the test chamber 38. An indicating cartridge 42 is removably disposed within the test chamber 38 for indicating by color an excessive amount of a contaminant contained within the test chamber 38.

Figure 2B:
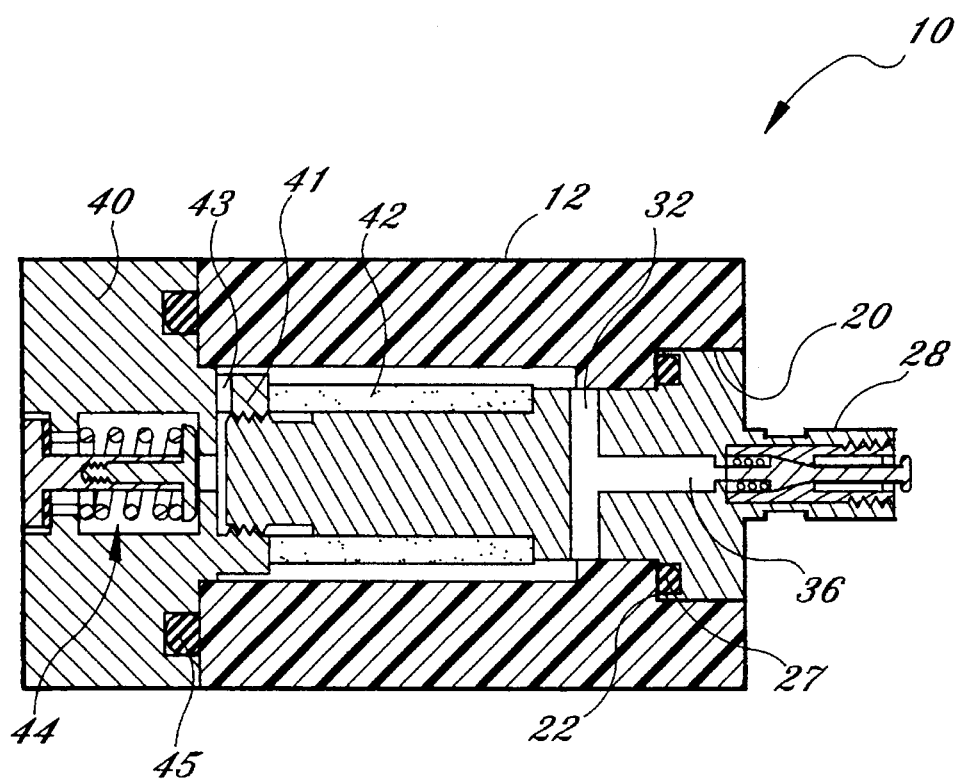

Referring now to FIGS. 1 and 2b, the preferred embodiment of a pressurized air tank air quality tester is shown generally at 10. As shown in FIG. 1, the apparatus comprises a housing 12 which, in the preferred embodiment, is substantially cylindrical and transparent. Though housing 12 is shown as being cylindrical in shape, such is not limiting, and it is well known that housings come in various shapes and sizes. As seen in FIG. 1, housing 12 has an inlet end 14 and an outlet end 16, the housing 12 having a receding neck portion 18 situated in the interior volume defined by the housing, the neck portion 18 defining a passageway therethrough. As seen in FIGS. 1 and 2b, the housing 12 includes a countersunk portion 20 forming a flange 22 proximal the inlet end 14 thereof, the flange 22 defining a first side of the neck portion 18. The apparatus further includes a multi-tiered mounting shaft generally designated by the reference numeral 24. The multi-tiered mounting shaft comprises a retaining hub 26 situated between opposite ends of the mounting shaft 24, a valve connector 28 integral with and disposed on one side of the retaining hub 26, a shank 30 of lesser width than the width of the retaining hub 26, the shank 30 extending inwardly from the side of the retaining hub 26 opposite to that of the valve connector side. The shank 30 comprises an aperture 32 therethrough and a rod 34 extending from the shank 30, the rod 34 being of a lesser width than the shank 30, wherein the free end of the rod 34 is threaded and defines one end of the mounting shaft 24. The mounting shaft 24 further defines a bore 36 extending from the valve connector 28 to the shank aperture 32 for fluidly communicating an outside pressurized air source with an interior test chamber 38 defined by the base member 40, the mounting shaft 24, and the housing 12 of the instant invention. The apparatus further comprises an indicating cartridge 42 removably mounted on the rod 34 for indicating by color the presence of an excessive amount of a given substance, such as carbon monoxide disposed within the interior test chamber 38. The base member 40 is connected to the outlet end of the housing 12, the base member 40 comprising a turret projection 41 integrally formed in and extending axially inwardly from the base member 40 and having a threaded aperture to engage the threaded end of the mounting shaft 24, the turret projection 41 being of lesser width than the base member 40. The turret projection 41 has a bore 43 therein for communicating the interior test chamber 38 with pressure relief valve 44. The pressure relief valve 44 is disposed in the base member 40 and comprises a threaded screw 46, a spring member 48, and a receiving member 50 for receiving the threaded screw 46 and the spring member 48, such that when the pressure inside the interior test chamber exceeds a predetermined value, the pressure relief valve 44 releases excess pressure from the interior test chamber 38. The multi-tiered mounting shaft 24 is constructed such that the retaining hub 26 is received by the flange 22 proximal the inlet end of the housing 12 and such that the aperture 32 of the shank 30 passes through the passageway in the neck portion 18, such that the top surface of the retaining hub 26 is substantially flush with the inlet end of the housing 12. An O-ring 27 is disposed on the bottom side of the retaining hub 26, thereby sealably engaging the retaining hub 26 with the flange 22. The base member 40 contains an O-ring 45 on an inner surface thereof for sealably engaging the base 40 to the outlet end of the housing 12.

To utilize the invention, one would attach the valve connector 28 of the instant invention to the pressurized air source (not shown) and then open the valve from the pressurized air source to allow a short stream of compressed air to enter the interior test chamber 38 via the valve connector 28, the bore 36 extending from the valve connector 28 to the shank 30, and shank aperture 32 which fluidly communicates the outside pressurized air source with interior test chamber 38. After a few seconds, the valve from the air source is closed, whereupon a sample of the air from the air source is trapped within the interior test chamber 38 along with the indicating cartridge 42. If the indicating cartridge 42 changes color, then the user is notified by the color change that an excessive amount of a given substance, such as carbon monoxide, is present within the test chamber 38 and also the compressed air source, therefore indicating that the compressed air source is contaminated and should not be used. The indicating cartridge 42 utilizes a known indicating, color change material or gel and may be used to indicate carbon monoxide or any other contaminant. The indicating cartridge 42 is removable and replaceable, and should be replaced preferably after ten to fifteen tests, or after contamination. The indicating cartridge 42 is replaced by unscrewing the base member 40 from the mounting shaft 24 and slidably removing the indicating cartridge 42 from the mounting shaft 24.

The instant invention has been shown and described herein in what is considered to be the most practical and preferred embodiment. It is recognized, however, that departures may be made therefrom within the scope of the invention and that obvious modifications will occur to a person skilled in the art.

What is claimed is:

1. An apparatus for testing air quality of a pressurized air source, comprising:

a housing having a longitudinal bore disposed therein, said housing having a first end and a second end;

said bore penetrating said first end and not penetrating said second end;

a closure disposed on said first end for sealing said housing and for forming an airtight test chamber therein;

a valve connector connected to said first end for fluidly communicating said air source with said test chamber; and an indicating cartridge removably disposed within said test chamber for indicating by color an excessive amount of a contaminant contained within said test chamber.

2. An apparatus as recited in claim 1, wherein said housing is transparent.

3. An apparatus for testing air quality of a pressurized air source, comprising:

a housing having a longitudinal bore disposed therein, said housing having a first end and a second end;

at least one closure disposed on at least one of said first end and said second end for sealing said housing and for forming an airtight test chamber therein;

a valve connector connected to said first end for fluidly communicating said air source with said test chamber; and an indicating cartridge removably disposed within said test chamber for indicating by color an excessive amount of a contaminant contained within said test chamber;

wherein said at least one closure comprises a first closure disposed on said first end and a second closure disposed on said second end;

wherein at least one of said closures comprises a base member having a turret projection.

4. An apparatus for testing air quality of a pressurized air source, comprising:

a housing having longitudinal bore disposed therein, said housing having a first end and a second end;

at least one closure disposed on at least one of said first end and said second end for sealing said housing and for forming an airtight test chamber therein;

a valve connector connected to said first end for fluidly communicating said air source with said test chamber; and an indicating cartridge removably disposed within said test chamber for indicating by color an excessive amount of a contaminant contained within said test chamber;

wherein said at least one closure comprises a first closure disposed on said first end and a second closure disposed on said second end;

wherein said first closure comprises a multi-tiered mounting shaft.

5. An apparatus as recited in claim 4, wherein said multi-tiered mounting shaft comprises:

a retaining hub situated between opposite ends of said mounting shaft, said retaining hub having a first side and a second side;

said valve connector being integral with said first side of said retaining hub;

a shank integral with said second side of said retaining hub, said shank including an aperture therethrough, said mounting shaft defining a bore extending from said valve connector to said shank aperture; and a rod integral with said shank and extending axially inward therefrom, said rod having a threaded end, said threaded end defining one end of said mounting shaft.

6. An apparatus as recited in claim 5, wherein said retaining hub includes an O-ring disposed on the second side thereof.

7. Apparatus for testing air quality of a pressurized air source comprising:

a housing having a longitudinal bore disposed therein, said housing having a first end and a second end;

at least one closure disposed on at least one of said first end and said second end for sealing said housing and for forming an airtight test chamber therein;

a valve connector connected to said first end for fluidly communicating said air source with said test chamber; and an indicating cartridge removably disposed within said test chamber for indicating by color an excessive amount of a contaminant contained within said test chamber;

wherein said at least one closure comprises a first closure disposed on said first end and a second closure disposed on said second end;

wherein said second closure comprises:

a base member comprising a turret projection having a threaded aperture therethrough.

8. An apparatus as recited in claim 7, wherein said base member further comprises a pressure relief valve disposed therein.

9. An apparatus as recited in claim 8, wherein said base member comprises an O-ring disposed on an inner surface thereof.

10. An apparatus as recited in claim 8, wherein said turret projection has a bore therein for communicating said test chamber with said pressure relief valve.

11. An apparatus for testing air quality of a pressurized air source, comprising:
   a housing having a longitudinal bore disposed therethrough, said housing having an inlet end and an outlet end, said housing further having a neck portion defining a passageway therethrough;
   a multi-tiered mounting shaft comprising:
      a retaining hub situated between opposite ends of said mounting shaft, said retaining hub having a first side and a second side;
      a valve connector integral with said first side of said retaining hub;
      a shank integral with said second side of said retaining hub, said shank including an aperture therethrough, said mounting shaft defining a bore extending from said valve connector to said shank aperture;
      a rod integral with said shank and extending axially inward therefrom, said rod having a threaded end, said threaded end defining one end of said mounting shaft;
   a base member connected to said outlet end of said housing, said base member comprising a turret projection having a threaded aperture therethrough for threadably engaging the threaded end of said rod, said base member further comprising a pressure relief valve disposed therein;
   an interior test chamber defined by said base member, said mounting shaft, and said neck portion, said interior test chamber being in fluid communication with said valve connector and with said pressure relief valve; and
   an indicating cartridge removably mounted on said rod for indicating by color an excessive amount of a contaminant contained within said interior test chamber;
   said shank aperture being in fluid communication with said mounting shaft bore, said shank aperture being disposed within said interior test chamber, such that air from the pressurized air source enters said interior test chamber via said valve connector, said mounting shaft bore, and said shank aperture.

12. An apparatus as recited in claim 11, wherein said retaining hub includes an O-ring disposed on the second side thereof for sealably engaging said retaining hub with said neck portion.

13. An apparatus as recited in claim 11, wherein said base member comprises an O-ring disposed on an inner surface thereof for sealably engaging said base member with the outlet end of said housing.

14. An apparatus as recited in claim 11, wherein said housing is substantially cylindrical.

15. An apparatus as recited in claim 11, wherein said turret projection has a bore therein for communicating said interior test chamber with said pressure relief valve.

16. An apparatus as recited in claim 11, wherein said housing is transparent.

* * * * *